United States Patent
Wachtel et al.

(10) Patent No.: US 7,973,032 B2
(45) Date of Patent: Jul. 5, 2011

(54) STAUROSPORINE DERIVATIVES FOR USE IN ALVEOLAR RHABDOMYOSARCOMA

(75) Inventors: Marco Wachtel, Zurich (CH); Beat W. Schäfer, Zurich (CH); Ralf Amstutz, Zurich (CH)

(73) Assignee: University of Zurich, Zurich (DE)

( * ) Notice: Subject to any disclaimer, the term of this patent is extended or adjusted under 35 U.S.C. 154(b) by 52 days.

(21) Appl. No.: 12/090,626

(22) PCT Filed: Nov. 13, 2006

(86) PCT No.: PCT/EP2006/068410
§ 371 (c)(1),
(2), (4) Date: Jun. 3, 2008

(87) PCT Pub. No.: WO2007/054579
PCT Pub. Date: May 18, 2007

(65) Prior Publication Data
US 2008/0280880 A1    Nov. 13, 2008

Related U.S. Application Data

(60) Provisional application No. 60/736,222, filed on Nov. 14, 2005.

(51) Int. Cl.
*A01N 43/00*     (2006.01)
*A61K 31/00*     (2006.01)
*A61K 31/553*    (2006.01)
*A61K 31/554*    (2006.01)

(52) U.S. Cl. .............................. 514/211.08; 514/211.09

(58) Field of Classification Search ............. 514/211.08, 514/211.09
See application file for complete search history.

(56) References Cited

U.S. PATENT DOCUMENTS

| | | | |
|---|---|---|---|
| 5,093,330 A | | 3/1992 | Caravatti et al. |
| 6,284,751 B1 | * | 9/2001 | Aiello et al. ................ 514/183 |
| 2003/0096875 A1 | | 5/2003 | Burton et al. ................ 514/703 |

FOREIGN PATENT DOCUMENTS

| | | | |
|---|---|---|---|
| WO | WO97/04761 | | 2/1997 |
| WO | WO 97/04761 | * | 2/1997 |
| WO | WO03/037347 | | 5/2003 |
| WO | WO 03/037347 | * | 5/2003 |
| WO | WO2004/112794 | | 12/2004 |
| WO | WO 2004/112794 | * | 12/2004 |
| WO | WO 2005/027971 | * | 3/2005 |
| WO | WO2005/027971 | | 3/2005 |

OTHER PUBLICATIONS

Bernasconi M, Remppis A, Fredericks WJ, Rauscher FJ 3rd, and Schäfer BW, "Induction of apoptosis in rhabdomyosarcoma cells through down-regulation of PAX proteins," Proceedings of the National Academy of Sciences, Nov. 1996, 93(23), 13164-13169.*
Bouché M, Zappelli F, Polimeni M, Adamo S, Wetsel WC, Senni MI, and Molinaro M, "Rapid activation and down-regulation of protein kinase C alpha in 12-O-Tetradecanoylphorbol-13-acetate-induced differentiation of human rhabdomyosarcoma cells," Cell Growth and Differentiation, Jul. 1995, 6(7), 845-852.*
Way D, Smith S, Sivendran S, Chie L, Kanovsky M, Brandt-Rauf PW, Chung DL, Michl J, and Pincus MR, "A protein kinase C inhibitor induces phenotypic reversion of ras-transformed pancreatic cancer cells and cooperatively blocks tumor cell proliferation with an anti-ras peptide," Cancer Chemotherapy and Pharmacology, Jun. 2002, 49(6), 429-437.*
Bernasconi et al., Induction of apoptosis in rhabdomyosarcoma cells through down-regulation of PAX proteins, Proc. Nat. Acad. Sci., USA, vol. 93, pp. 13164-13169 (1996).

* cited by examiner

*Primary Examiner* — Sam-ming Hui
*Assistant Examiner* — Paul Zarek
(74) *Attorney, Agent, or Firm* — George R. Dohmann

(57) ABSTRACT

This invention relates to staurosporine derivatives are effective when used in combination with ionizing radiation for the delay of progression or treatment of a proliferative disease, especially a disease associated with a PAX/FKHR translocation including a PAX3/FKHR translocation and a PAX7/FKHR translocation, more especially a solid tumor disease such as a Sarcoma, most especially an Alveolar Rhabdomyosarcoma.

3 Claims, No Drawings

STAUROSPORINE DERIVATIVES FOR USE IN ALVEOLAR RHABDOMYOSARCOMA

This application claims benefit of U.S. provisional Application 60/736,222, filed Nov. 14, 2005, the contents of this application is incorporated herein in its entirety.

This invention relates to organic compounds, in particular to pharmaceutical compositions for use for the delay of progression or treatment of a proliferative disease, especially a disease associated with a PAX/FKHR translocation, especially a Sarcoma, especially Alveolar Rhabdomyosarcoma.

We have now found that certain the FLT-3 inhibitors, especially staurosporine derivatives, are effective when used in the treatment of a disease associated with a PAX/FKHR translocation, especially of a disease associated with PAX/FKHR expression, most especially of Pediatric sarcoma alveolar rhabdomyosarcoma ("aRMS"). In one embodiment, aRMS expresses the chimaeric fusion protein PAX3/FKHR due to a chromosomal translocation event t(2; 13). In another embodiment, aRMS expresses the chimaeric fusion protein PAX7/FKHR due to a chromosomal translocation event t(1; 13). See Mendelian Inheritance in Man accno. #268220.

Accordingly the invention provides a method for the delay of progression or treatment of a proliferative disease, especially a disease associated with a PAX/FKHR translocation, especially a Sarcoma, more especially a Alveolar Rhabdomyosarcoma, in a subject in need of such treatment, wherein such treatment comprises administering to the subject an effective amount of a staurosporine derivatives of formula

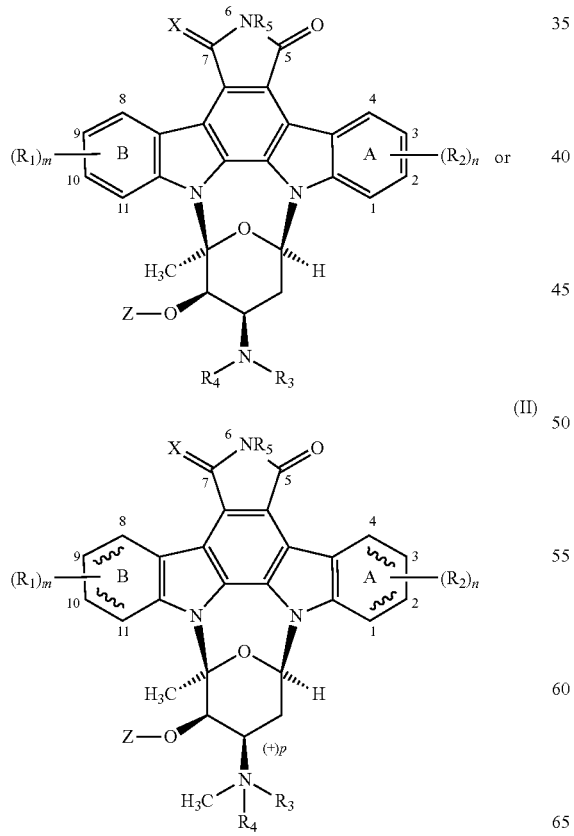

wherein (II) is the partially hydrogenated derivative of compound (I),

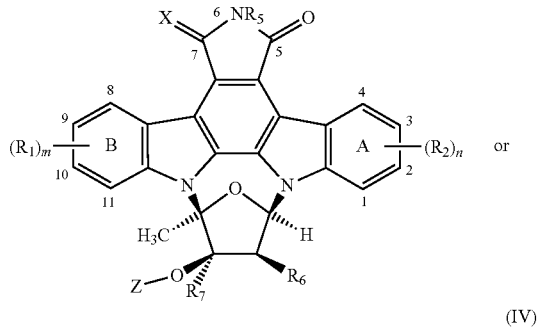

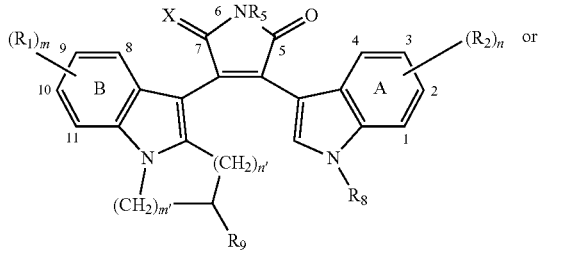

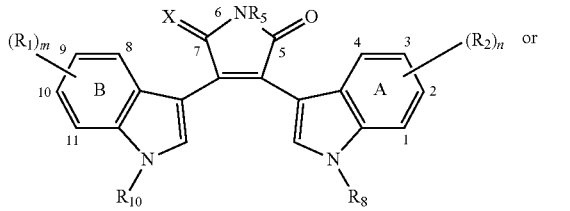

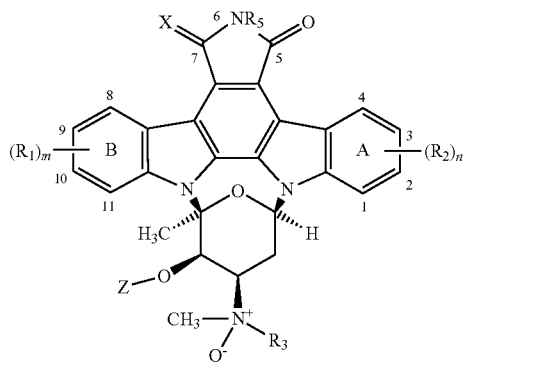

wherein $R_1$ and $R_2$, are, independently of one another, unsubstituted or substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

n and m are, independently of one another, a number from and including 0 to and including 4;

n' and m' are, independently of one another, a number from and including 0 to and including 4;

R₃, R₄, R₈ and R₁₀ are, independently of one another, hydrogen, —O⁻, acyl with up to 30 carbon atoms, an aliphatic, carbocyclic, or carbocyclic-aliphatic radical with up to 29 carbon atoms in each case, a heterocyclic or heterocyclic-aliphatic radical with up to 20 carbon atoms in each case, and in each case up to 9 heteroatoms, an acyl with up to 30 carbon atoms, wherein R₄ may also be absent;

or if R₃ is acyl with up to 30 carbon atoms, R₄ is not an acyl;

p is 0 if R₄ is absent, or is 1 if R₃ and R₄ are both present and in each case are one of the aforementioned radicals;

R₅ is hydrogen, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms;

R₇, R₆ and R₉ are acyl or -(lower alkyl)-acyl, unsubstituted or substituted alkyl, hydrogen, halogen, hydroxy, etherified or esterified hydroxy, amino, mono- or disubstituted amino, cyano, nitro, mercapto, substituted mercapto, carboxy, carbonyl, carbonyldioxy, esterified carboxy, carbamoyl, N-mono- or N,N-di-substituted carbamoyl, sulfo, substituted sulfonyl, aminosulfonyl or N-mono- or N,N-di-substituted aminosulfonyl;

X stands for 2 hydrogen atoms; for 1 hydrogen atom and hydroxy; for O; or for hydrogen and lower alkoxy;

Z stands for hydrogen or lower alkyl;

and either the two bonds characterised by wavy lines are absent in ring A and replaced by 4 hydrogen atoms, and the two wavy lines in ring B each, together with the respective parallel bond, signify a double bond;

or the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present.

The general terms and definitions used hereinbefore and hereinafter preferably have the following meanings for the staurosporine derivatives:

The prefix "lower" indicates that the associated radical preferably has up to and including a maximum of 7 carbon atoms, especially up to and including a maximum of 4 carbon atoms.

Lower alkyl is especially methyl, ethyl, n-propyl, isopropyl, n-butyl, isobutyl, sec-butyl, or tert-butyl, and also pentyl, hexyl, or heptyl.

Unsubstituted or substituted alkyl is preferably $C_1$-$C_{20}$alkyl, especially lower alkyl, typically methyl, ethyl, n-propyl, isopropyl, n-butyl, isobutyl, sec-butyl, or tert-butyl, which is unsubstituted or substituted especially by halogen, such as fluorine, chlorine, bromine, or iodine, $C_6$-$C_{14}$aryl, such as phenyl or naphthyl, hydroxy, etherified hydroxy, such as lower alkoxy, phenyl-lower alkoxy or phenyloxy, esterified hydroxy, such as lower alkanoyloxy or benzoyloxy, amino, mono- or disubstituted amino, such as lower alkylamino, lower alkanoylamino, phenyl-lower alkylamino, N,N-di-lower alkylamino, N,N-di-(phenyl-lower alkyl)amino, cyano, mercapto, substituted mercapto, such as lower alkylthio, carboxy, esterified carboxy, such as lower alkoxycarbonyl, carbamoyl, N-mono- or N,N-disubstituted carbamoyl, such as N-lower alkylcarbamoyl or N,N-di-lower alkylcarbamoyl, sulfo, substituted sulfo, such as lower alkanesulfonyl or lower alkoxysulfonyl, aminosulfonyl or N-mono- or N,N-disubstituted aminosulfonyl, such as N-lower alkylaminosulfonyl or N,N-di-lower alkylaminosulfonyl.

Halogen is preferably fluorine, chlorine, bromine, or iodine, especially fluorine or chlorine.

Etherified hydroxy is especially lower alkoxy, $C_6$-$C_{14}$aryloxy, such as phenyloxy, or $C_6$-$C_{14}$aryl-lower alkoxy, such as benzyloxy.

Esterified hydroxy is preferably lower alkanoyloxy or $C_6$-$C_{14}$arylcarbonyloxy, such as benzoyloxy.

Mono- or disubstituted amino is especially amino mono-substituted or disubstituted by lower alkyl, $C_6$-$C_{14}$aryl, $C_6$-$C_{14}$aryl-lower alkyl, lower alkanoyl, or $C_6$-$C_{12}$arylcarbonyl.

Substituted mercapto is especially lower alkylthio, $C_6$-$C_{14}$arylthio, $C_6$-$C_{14}$aryl-lower alkylthio, lower alkanoylthio, or $C_6$-$C_{14}$aryl-lower alkanoylthio.

Esterified carboxy is especially lower alkoxycarbonyl, $C_6$-$C_{14}$aryl-lower alkoxy-carbonyl or $C_6$-$C_{14}$aryloxycarbonyl.

N-Mono- or N,N-disubstituted carbamoyl is especially carbamoyl N-monosubstituted or N,N-disubstituted by lower alkyl, $C_6$-$C_{14}$aryl or $C_6$-$C_{14}$aryl-lower alkyl.

Substituted sulfonyl is especially $C_6$-$C_{14}$arylsulfonyl, such as toluenesulfonyl, $C_6$-$C_{14}$aryl-lower alkanesulfonyl or lower alkanesulfonyl.

N-Mono- or N,N-disubstituted aminosulfonyl is especially aminosulfonyl N-monosubstituted or N,N-disubstituted by lower alkyl, $C_6$-$C_{14}$aryl or $C_6$-$C_{14}$aryl-lower alkyl.

$C_6$-$C_{14}$Aryl is an aryl radical with 6 to 14 carbon atoms in the ring system, such as phenyl, naphthyl, fluorenyl, or indenyl, which is unsubstituted or is substituted especially by halogen, such as fluorine, chlorine, bromine, or iodine, phenyl or naphthyl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl) amino, cyano, mercapto, lower alkylthio, carboxy, lower alkoxycarbonyl, carbamoyl, N-lower alkylcarbamoyl, N,N-di-lower alkylcarbamoyl, sulfo, lower alkanesulfonyl, lower alkoxysulfonyl, aminosulfonyl, N-lower alkylaminosulfonyl, or N,N-di-lower alkylaminosulfonyl.

The indices n and m are in each case preferably 1, 2 or especially 0. In general, compounds of formula I in which n and m are in each case 0 (zero) are especially preferred.

An aliphatic carbohydrate radical R₃, R₄, R₈ or R₁₀ with up to 29 carbon atoms, which is substituted by acyclic substituents and preferably has a maximum of 18, especially a maximum of 12, and as a rule not more than 7 carbon atoms, may be saturated or unsaturated and is especially an unsubstituted or a straight-chain or branched lower alkyl, lower alkenyl, lower alkadienyl, or lower alkinyl radical substituted by acyclic substituents. Lower alkyl is, for example, methyl, ethyl, n-propyl, isopropyl, n-butyl, isobutyl, sec-butyl or tert-butyl, and also n-pentyl, isopentyl, n-hexyl, isohexyl and n-heptyl; lower alkenyl is, for example, allyl, propenyl, isopropenyl, 2- or 3-methallyl and 2- or 3-butenyl; lower alkadienyl is, for example, 1-penta-2,4-dienyl; lower alkinyl is, for example, propargyl or 2-butinyl. In corresponding unsaturated radicals, the double bond is especially located in a position higher than the α-position in relation to the free valency. Substituents are especially the acyl radicals defined hereinbelow as substituents of R°, preferably free or esterified carboxy, such as carboxy or lower alkoxycarbonyl, cyano or di-lower alkylamino.

A carbocyclic or carbocyclic-aliphatic radical R₃, R₄, R₈ or R₁₀ with up to 29 carbon atoms in each case is especially an aromatic, a cycloaliphatic, a cycloaliphatic-aliphatic, or an aromatic-aliphatic radical which is either present in unsubstituted form or substituted by radicals referred to hereinbelow as substituents of $R^o$. An aromatic radical (aryl radical) $R_3$ or $R_4$ is most especially a phenyl, also a naphthyl, such as 1- or 2-naphthyl, a biphenylyl, such as especially 4-biphenylyl, and also an anthryl, fluorenyl and azulenyl, as well as their aromatic analogues with one or more saturated rings, which is either present in unsubstituted form or substituted by radicals referred to hereinbelow as substituents of $R^o$. Preferred aromatic-aliphatic radicals are aryl-lower alkyl- and aryl-lower alkenyl radicals, e.g. phenyl-lower alkyl or phenyl-lower alkenyl with a terminal phenyl radical, such as for example benzyl, phenethyl, 1-, 2-, or 3-phenylpropyl, diphenylmethyl (benzhydryl), trityl, and cinnamyl, and also 1- or 2-naphthylmethyl. Of aryl radicals carrying acyclic radicals, such as lower alkyl, special mention is made of o-, m- and p-tolyl and xylyl radicals with variously situated methyl radicals.

A cycloaliphatic radical $R_3$, $R_4$, $R_8$ or $R_{10}$ with up to 29 carbon atoms is especially a substituted or preferably unsubstituted mono-, bi-, or polycyclic cycloalkyl-, cycloalkenyl-, or cycloalkadienyl radical. Preference is for radicals with a maximum of 14, especially 12, ring-carbon atoms and 3- to 8-, preferably 5- to 7-, and most especially 6-member rings which can also carry one or more, for example two, aliphatic hydrocarbon radicals, for example those named above, especially the lower alkyl radicals, or other cycloaliphatic radicals as substituents. Preferred substituents are the acyclic substituents named hereinbelow for $R^o$.

A cycloaliphatic-aliphatic radical $R_3$, $R_4$, $R_8$ or $R_{10}$ with up to 29 carbon atoms is a radical in which an acyclic radical, especially one with a maximum of 7, preferably a maximum of 4 carbon atoms, such as especially methyl, ethyl, and vinyl, carries one or more cycloaliphatic radicals as defined hereinabove. Special mention is made of cycloalkyl-lower-alkyl radicals, as well as their analogues which are unsaturated in the ring and/or in the chain, but are non-aromatic, and which carry the ring at the terminal carbon atom of the chain. Preferred substituents are the acyclic substituents named herein below for $R^o$.

Heterocyclic radicals $R_3$, $R_4$, $R_8$ or $R_{10}$ with up to 20 carbon atoms each and up to 9 heteroatoms each are especially monocyclic, but also bi- or polycyclic, aza-, thia-, oxa-, thiaza-, oxaza-, diaza-, triaza-, or tetrazacyclic radicals of an aromatic character, as well as corresponding heterocyclic radicals of this type which are partly or most especially wholly saturated, these radicals—if need be—possibly carrying further acyclic, carbocyclic, or heterocyclic radicals and/or possibly mono-, di-, or polysubstituted by functional groups, preferably those named hereinabove as substituents of aliphatic hydrocarbon radicals. Most especially they are unsubstituted or substituted monocyclic radicals with a nitrogen, oxygen, or sulfur atom, such as 2-aziridinyl, and especially aromatic radicals of this type, such as pyrryl, for example 2-pyrryl or 3-pyrryl, pyridyl, for example 2-, 3-, or 4-pyridyl, and also thienyl, for example 2- or 3-thienyl, or furyl, for example 2-furyl; analogous bicyclic radicals with an oxygen, sulfur, or nitrogen atom are, for example, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, or benzothienyl, typically 2- or 3-benzothienyl; preferred monocyclic and bicyclic radicals with several heteroatoms are, for example, imidazolyl, typically 2- or 4-imidazolyl, pyrimidinyl, typically 2- or 4-pyrimidinyl, oxazolyl, typically 2-oxazolyl, isoxazolyl, typically 3-isoxazolyl, or thiazolyl, typically 2-thiazolyl, and benzimidazolyl, typically 2-benzimidazolyl, benzoxazolyl, typically 2-benzoxazolyl, or quinazolyl, typically 2-quinazolinyl. Appropriate partially or, especially, completely saturated analogous radicals may also be considered, such as 2-tetrahydrofuryl, 2- or 3-pyrrolidinyl, 2-, 3-, or 4-piperidyl, and also 2- or 3-morpholinyl, 2- or 3-thiomorpholinyl, 2-piperazinyl and N-mono- or N,N'-bis-lower alkyl-2-piperazinyl radicals. These radicals may also carry one or more acyclic, carbocyclic, or heterocyclic radicals, especially those mentioned hereinabove. The free valency of the heterocyclic radicals $R_3$ or $R_4$ must emanate from one of their carbon atoms. Heterocyclyl may be unsubstituted or substituted by one or more, preferably one or two, of the substituents named hereinbelow for $R^o$.

Heterocyclic-aliphatic radicals $R_3$, $R_4$, $R_8$ or $R_{10}$ especially lower alkyl radicals, especially with a maximum of 7, preferably a maximum of 4 carbon atoms, for example those named hereinabove, which carry one, two, or more heterocyclic radicals, for example those named in the preceding paragraph, the heterocyclic ring possibly being linked to the aliphatic chain also by one of its nitrogen atoms. A preferred heterocyclic-aliphatic radical $R_1$ is, for example, imidazol-1-ylmethyl, 4-methylpiperazin-1-ylmethyl, piperazin-1-ylmethyl, 2-(morpholin-4-yl)ethyl and also pyrid-3-ylmethyl. Heterocyclyl may be unsubstituted or substituted by one or more, preferably one or two, of the substituents named hereinbelow for $R^o$.

A heteroaliphatic radical $R_3$, $R_4$, $R_8$ or $R_{10}$ with up to 20 carbon atoms each and up to 10 heteroatoms each is an aliphatic radical which, instead of one, two, or more carbon atoms, contains identical or different heteroatoms, such as especially oxygen, sulfur, and nitrogen. An especially preferred arrangement of a heteroaliphatic radical $R_1$ takes the form of oxa-alkyl radicals in which one or more carbon atoms are replaced in a preferably linear alkyl by oxygen atoms preferably separated from one another by several (especially 2) carbon atoms so that they form a repeating group, if need be multi-repeating group $(O-CH_2-CH_2-)_q$, wherein q=1 to 7.

Especially preferred as $R_3$, $R_4$, $R_8$ or $R_{10}$, apart from acyl, is lower alkyl, particularly methyl or ethyl; lower alkoxycarbonyl-lower alkyl, especially methoxycarbonylmethyl or 2-(tert-butoxycarbonyl)ethyl; carboxy-lower alkyl, especially carboxymethyl or 2-carboxyethyl; or cyano-lower alkyl, especially 2-cyanoethyl.

An acyl radical $R_3$, $R_4$, $R_6$, $R_7$, $R_8$, $R_9$, or $R_{10}$ with up to 30 carbon atoms derives from a carboxylic acid, functionally modified if need be, an organic sulfonic acid, or a phosphoric acid, such as pyro- or orthophosphoric acid, esterified if need be.

An acyl designated $Ac^1$ and derived from a carboxylic acid, functionally modified if need be, is especially one of the subformula $Y-C(=W)-$, wherein W is oxygen, sulfur, or imino and Y is hydrogen, hydrocarbyl $R^o$ with up to 29 carbon atoms, hydrocarbyloxy $R^o-O-$, an amino group or a substituted amino group, especially one of the formula $R^oHN-$ or $R^oR^oN-$ (wherein the $R^o$ radicals may be identical or different from one another).

The hydrocarbyl (hydrocarbon radical) $R^o$ is an acyclic (aliphatic), carbocyclic, or carbocyclic-acyclic hydrocarbon radical, with up to 29 carbon atoms each, especially up to 18, and preferably up to 12 carbon atoms, and is saturated or unsaturated, unsubstituted or substituted. Instead of one, two, or more carbon atoms, it may contain identical or different heteroatoms, such as especially oxygen, sulfur, and nitrogen in the acyclic and/or cyclic part; in the latter case, it is described as a heterocyclic radical (heterocyclyl radical) or a heterocyclic-acyclic radical.

Unsaturated radicals are those, which contain one or more, especially conjugated and/or isolated, multiple bonds (double or triple bonds). The term cyclic radicals includes also aromatic and non-aromatic radicals with conjugated double bonds, for example those wherein at least one 6-member carbocyclic or a 5- to 8-member heterocyclic ring contains the maximum number of non-cumulative double bonds. Carbocyclic radicals, wherein at least one ring is present as a 6-member aromatic ring (i.e. a benzene ring), are defined as aryl radicals.

An acyclic unsubstituted hydrocarbon radical $R^o$ is especially a straight-chained or branched lower alkyl-, lower alkenyl-, lower alkadienyl-, or lower alkinyl radical. Lower alkyl $R^o$ is, for example, methyl, ethyl, n-propyl, isopropyl, n-butyl, isobutyl, sec-butyl or tert-butyl, and also n-pentyl, isopentyl, n-hexyl, isohexyl and n-heptyl; lower alkenyl is, for example, allyl, propenyl, isopropenyl, 2- or 3-methallyl and 2- or 3-butenyl; lower alkadienyl is, for example, 1-penta-2,4-dienyl; lower alkinyl is, for example, propargyl or 2-butinyl. In corresponding unsaturated radicals, the double bond is especially located in a position higher than the α-position in relation to the free valency.

A carbocyclic hydrocarbon radical $R^o$ is especially a mono-, bi-, or polycyclic cycloalkyl-, cycloalkenyl-, or cycloalkadienyl radical, or a corresponding aryl radical. Preference is for radicals with a maximum of 14, especially 12, ring-carbon atoms and 3- to 8-, preferably 5- to 7-, and most especially 6-member rings which can also carry one or more, for example two, acyclic radicals, for example those named above, especially the lower alkyl radicals, or other carbocyclic radicals. Carbocyclic-acyclic radicals are those in which an acyclic radical, especially one with a maximum of 7, preferably a maximum of 4 carbon atoms, such as especially methyl, ethyl and vinyl, carries one or more carbocyclic, if need be aromatic radicals of the above definition. Special mention is made of cycloalkyl-lower and aryl-lower alkyl radicals, as well as their analogues which are unsaturated in the ring and/or chain, and which carry the ring at the terminal carbon atom of the chain.

Cycloalkyl $R^o$ has most especially from 3 up to and including 10 carbon atoms and is, for example, cyclopropyl, cyclobutyl, cyclopentyl, cyclohexyl, cycloheptyl, and cyclooctyl, as well as bicyclo[2,2,2]octyl, 2-bicyclo[2,2,1] heptyl, and adamantyl, which may also be substituted by 1, 2, or more, for example lower, alkyl radicals, especially methyl radicals; cycloalkenyl is for example one of the monocyclic cycloalkyl radicals already named which carries a double bond in the 1-, 2-, or 3 position. Cycloalkyl-lower alkyl or -lower alkenyl is for example a -methyl, -1- or -2-ethyl, -1- or -2-vinyl, -1-, -2-, or -3-propyl or -allyl substituted by one of the above-named cycloalkyl radicals, those substituted at the end of the linear chain being preferred.

An aryl radical $R^0$ is most especially a phenyl, also a naphthyl, such as 1- or 2-naphthyl, a biphenylyl, such as especially 4-biphenylyl, and also an anthryl, fluorenyl and azulenyl, as well as their aromatic analogues with one or more saturated rings. Preferred aryl-lower alkyl and -lower alkenyl radicals are, for example, phenyl-lower alkyl or phenyl-lower alkenyl with a terminal phenyl radical, such as for example benzyl, phenethyl, 1-, 2-, or 3-phenylpropyl, diphenylmethyl (benzhydryl), trityl, and cinnamyl, and also 1- or 2-naphthylmethyl. Aryl may be unsubstituted or substituted.

Heterocyclic radicals, including heterocyclic-acyclic radicals, are especially monocyclic, but also bi- or polycyclic, aza-, thia-, oxa-, thiaza-, oxaza-, diaza-, triaza-, or tetrazacyclic radicals of an aromatic character, as well as corresponding heterocyclic radicals of this type which are partly or most especially wholly saturated; if need be, for example as in the case of the above-mentioned carbocyclic or aryl radicals, these radicals may carry further acyclic, carbocyclic, or heterocyclic radicals and/or may be mono-, di-, or polysubstituted by functional groups. The acyclic part in heterocyclic-acyclic radicals has for example the meaning indicated for the corresponding carbocyclic-acyclic radicals. Most especially they are unsubstituted or substituted monocyclic radicals with a nitrogen, oxygen, or sulfur atom, such as 2-aziridinyl, and especially aromatic radicals of this type, such as pyrrolyl, for example 2-pyrrolyl or 3-pyrrolyl, pyridyl, for example 2-, 3-, or 4-pyridyl, and also thienyl, for example 2- or 3-thienyl, or furyl, for example 2-furyl; analogous bicyclic radicals with an oxygen, sulfur, or nitrogen atom are, for example, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, or benzothienyl, typically 2- or 3-benzothienyl; preferred monocyclic and bicyclic radicals with several heteroatoms are, for example, imidazolyl, typically 2-imidazolyl, pyrimidinyl, typically 2- or 4-pyrimidinyl, oxazolyl, typically 2-oxazolyl, isoxazolyl, typically 3-isoxazolyl, or thiazolyl, typically 2-thiazolyl, and benzimidazolyl, typically 2-benzimidazolyl, benzoxazolyl, typically 2-benzoxazolyl, or quinazolyl, typically 2-quinazolinyl. Appropriate partially or, especially, completely saturated analogous radicals may also be considered, such as 2-tetrahydrofuryl, 4-tetrahydrofuryl, 2- or 3-pyrrolidyl, 2-, 3-, or 4-piperidyl, and also 2- or 3-morpholinyl, 2- or 3-thiomorpholinyl, 2-piperazinyl, and N,N'-bis-lower alkyl-2-piperazinyl radicals. These radicals may also carry one or more acyclic, carbocyclic, or heterocyclic radicals, especially those mentioned hereinabove. Heterocyclic-acyclic radicals are especially derived from acyclic radicals with a maximum of 7, preferably a maximum of 4 carbon atoms, for example those named hereinabove, and may carry one, two, or more heterocyclic radicals, for example those named hereinabove, the ring possibly being linked to the aliphatic chain also by one of its nitrogen atoms.

As already mentioned, a hydrocarbyl (including a heterocyclyl) may be substituted by one, two, or more identical or different substituents (functional groups); one or more of the following substituents may be considered: lower alkyl; free, etherified and esterified hydroxyl groups; carboxy groups and esterified carboxy groups; mercapto- and lower alkylthio- and, if need be, substituted phenylthio groups; halogen atoms, typically chlorine and fluorine, but also bromine and iodine; halogen-lower alkyl groups; oxo groups which are present in the form of formyl (i.e. aldehydro) and keto groups, also as corresponding acetals or ketals; azido groups; nitro groups; cyano groups; primary, secondary and preferably tertiary amino groups, amino-lower alkyl, mono- or disubstituted amino-lower alkyl, primary or secondary amino groups protected by conventional protecting groups (especially lower alkoxycarbonyl, typically tert-butoxycarbonyl) lower alkylenedioxy, and also free or functionally modified sulfo groups, typically sulfamoyl or sulfo groups present in free form or as salts. The hydrocarbyl radical may also carry carbamoyl, ureido, or guanidino groups, which are free or which carry one or two substituents, and cyano groups. The above use of the word "groups" is taken to imply also an individual group.

Halogen-lower alkyl contains preferably 1 to 3 halogen atoms; preferred is trifluoromethyl or chloromethyl.

An etherified hydroxyl group present in the hydrocarbyl as substituent is, for example, a lower alkoxy group, typically the methoxy-, ethoxy-, propoxy-, isopropoxy-, butoxy-, and tert-butoxy group, which may also be substituted, especially by (i) heterocyclyl, whereby heterocyclyl can have preferably 4 to 12 ring atoms, may be unsaturated, or partially or wholly saturated, is mono- or bicyclic, and may contain up to three heteroatoms selected from nitrogen, oxygen, and sulfur, and is most especially pyrrolyl, for example 2-pyrrolyl or 3-pyrrolyl, pyridyl, for example 2-, 3- or 4-pyridyl, and also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl; and also (ii) by halogen atoms, for example mono-, di-, or polysubstituted especially in the 2-position, as in the 2,2,2-trichloroethoxy, 2-chloroethoxy, or 2-iodoethoxy radical, or (iii) by hydroxy or (iv) lower alkoxy radicals, each preferably monosubstituted, especially in the 2-position, as in the 2-methoxyethoxy radical. Such etherified hydroxyl groups are also unsubstituted or substituted phenoxy radicals and phenyl-lower alkoxy radicals, such as especially benzyloxy, benzhydryloxy, and triphenylmethoxy (trityloxy), as well as heterocyclyloxy radicals, wherein heterocyclyl can have preferably 4 to 12 ring atoms, may be unsaturated, or partially or wholly saturated, is mono- or bicyclic, and may contain up to three heteroatoms selected from nitrogen, oxygen, and sulfur, and is most especially pyrrolyl, for example 2-pyrrolyl or 3-pyrrolyl, pyridyl, for example 2-, 3- or 4-pyridyl, and also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl; such as especially 2- or 4-tetrahydropyranyloxy.

Etherified hydroxyl groups in this context are taken to include silylated hydroxyl-groups, typically for example tri-lower alkylsilyloxy, typically trimethylsilyloxy and dimethyl-tert-butylsilyloxy, or phenyldi-lower alkylsilyloxy and lower alkyl-diphenylsilyloxy.

An esterified hydroxyl group present in the hydrocarbyl as a substituent is, for example, lower alkanoyloxy.

A carboxyl group present in the hydrocarbyl as a substituent is one in which the hydrogen atom is replaced by one of the hydrocarbyl radicals characterised hereinabove, preferably a lower alkyl- or phenyl-lower alkyl radical; an example of an esterified carboxyl group is lower alkoxycarbonyl or phenyl-lower alkoxycarbonyl substituted if need be in the phenyl part, especially the methoxy, ethoxy, tert-butoxy, and benzyloxycarbonyl group, as well as a lactonised carboxyl group.

A primary amino group —NH$_2$ as substituent of the hydrocarbyls may also be present in a form protected by a conventional protecting group. A secondary amino group carries, instead of one of the two hydrogen atoms, a hydrocarbyl radical, preferably an unsubstituted one, typically one of the above-named, especially lower alkyl, and may also be present in protected form.

A tertiary amino group present in the hydrocarbyl as substituent carries 2 different or, preferably, identical hydrocarbyl radicals (including the heterocyclic radicals), such as the unsubstituted hydrocarbyl radicals characterised hereinabove, especially lower alkyl.

A preferred amino group is one with the formula $R_{11}(R_{12})$N—, wherein $R_{11}$ and $R_{12}$ are independently in each case hydrogen, unsubstituted acyclic $C_1$-$C_7$-hydrocarbyl (such as especially $C_1$-$C_4$alkyl or $C_2$-$C_4$alkenyl) or monocyclic aryl, aralkyl, or aralkenyl, substituted if necessary by $C_1$-$C_4$-alkyl, $C_1$-$C_4$-alkoxy, halogen, and/or nitro, and having a maximum of 10 carbon atoms, where the carbon-containing radicals may be interlinked through a carbon-carbon bond or an oxygen atom, a sulfur atom, or a nitrogen atom substituted if necessary by hydrocarbyl. In such a case, they form a nitrogen-containing heterocyclic ring with the nitrogen atom of the amino group. The following are examples of especially preferred disubstituted amino groups: di-lower alkylamino, typically dimethylamino or diethylamino, pyrrolidino, imidazol-1-yl, piperidino, piperazino, 4-lower alkylpiperazino, morpholino, thiomorpholino and piperazino or 4-methylpiperazino, as well as diphenylamino and dibenzylamino substituted if need be, especially in the phenyl part, for example by lower-alkyl, lower-alkoxy, halogen, and/or nitro; of the protected groups, especially lower alkoxycarbonylamino, typically tert-butoxycarbonylamino, phenyl-lower alkoxycarbonylamino, typically 4-methoxybenzyloxycarbonylamino, and 9-fluorenylmethoxycarbonylamino.

Amino-lower alkyl is most especially substituted in the 1-position of the lower alkyl chain by amino and is especially aminomethyl.

Mono- or disubstituted amino-lower alkyl is amino-lower alkyl substituted by one or two radicals, wherein amino-lower alkyl is most especially substituted by amino in the 1-position of the lower alkyl chain and is especially aminomethyl; the amino substituents here are preferably (if 2 substituents are present in the respective amino group independently of one another) from the group comprising lower alkyl, such as especially methyl, ethyl or n-propyl, hydroxy-lower alkyl, typically 2-hydroxyethyl, $C_3$-$C_8$cycloalkyl, especially cyclohexyl, amino-lower alkyl, typically 3-aminopropyl or 4-aminobutyl, N-mono- or N,N-di(lower alkyl)-amino-lower alkyl, typically 3-(N,N-dimethylamino)propyl, amino, N-mono- or N,N-di-lower alkylamino and N-mono- or N,N-di-(hydroxy-lower alkyl)amino.

Disubstituted amino-lower alkyl is also a 5 or 6-membered, saturated or unsaturated heterocyclyl bonded to lower alkyl via a nitrogen atom (preferably in the 1-position) and having 0 to 2, especially 0 or 1, other heteroatoms selected from oxygen, nitrogen, and sulfur, which is unsubstituted or substituted, especially by one or two radicals from the group comprising lower alkyl, typically methyl, and also oxo. Preferred here is pyrrolidino (1-pyrrolidinyl), piperidino (1-piperidinyl), piperazino (1-piperazinyl), 4-lower alkylpiperazino, typically 4-methylpiperazino, imidazolino (1-imidazolyl), morpholino (4-morpholinyl), or also thiomorpholino, S-oxo-thiomorpholino, or S,S-dioxothiomorpholino.

Lower alkylenedioxy is especially methylenedioxy.

A carbamoyl group carrying one or two substituents is especially aminocarbonyl (carbamoyl) which is substituted by one or two radicals at the nitrogen; the amino substituents here are preferably (if 2 substituents are present in the respective amino group independently of one another) from the group comprising lower alkyl, such as especially methyl, ethyl or n-propyl, hydroxy-lower alkyl, typically 2-hydroxyethyl, $C_3$-$C_8$cycloalkyl, especially cyclohexyl, amino-lower alkyl, typically 3-aminopropyl or 4-aminobutyl, N-mono- or N,N-di(lower alkyl)-amino-lower alkyl, typically 3-(N,N-dimethylamino)propyl, amino, N-mono- or N,N-di-lower alkylamino and N-mono- or N,N-di-(hydroxy-lower alkyl) amino; disubstituted amino in aminocarbamoyl is also a 5 or 6-membered, saturated or unsaturated heterocyclyl with a bonding nitrogen atom and 0 to 2, especially 0 or 1, other heteroatoms selected from oxygen, nitrogen, and sulfur, which is unsubstituted or substituted, especially by one or two radicals from the group comprising lower alkyl, typically methyl, and also oxo. Preferred here is pyrrolidino (1-pyrrolidinyl), piperidino (1-piperidinyl), piperazino (1-piperazinyl), 4-lower alkylpiperazino, typically 4-methylpiperazino, imidazolino (1-imidazolyl), morpholino (4-morpholinyl), or also thiomorpholino, S-oxo-thiomorpholino, or S,S-dioxothiomorpholino.

An acyl derived from an organic sulfonic acid, which is designated $Ac^2$, is especially one with the subformula $R^o$—$SO_2$—, wherein $R^o$ is a hydrocarbyl as defined above in the general and specific meanings, the latter also being generally preferred here. Especially preferred is lower alkylphenylsulfonyl, especially 4-toluenesulfonyl.

An acyl derived from a phosphoric acid, esterified if necessary, which is designated $Ac^3$, is especially one with the subformula $R^oO(R^oO)P(=O)$—, wherein the radicals $R^o$ are, independently of one another, as defined in the general and specific meanings indicated above.

Reduced data on substituents given hereinbefore and hereinafter are considered to be preferences.

Preferred compounds according to the invention are, for example, those wherein $R^0$ has the following preferred meanings: lower alkyl, especially methyl or ethyl, amino-lower alkyl, wherein the amino group is unprotected or is protected by a conventional amino protecting group—especially by lower alkoxycarbonyl, typically tert-lower alkoxycarbonyl, for example tert-butoxycarbonyl—e.g. aminomethyl, R,S-, R- or preferably S-1-aminoethyl, tert-butoxycarbonylaminomethyl or R,S-, R-, or preferably S-1-(tert-butoxycarbonylamino)ethyl, carboxy-lower alkyl, typically 2-carboxyethyl, lower alkoxycarbonyl-lower alkyl, typically 2-(tert-butoxycarbonyl)ethyl, cyano-lower alkyl, typically 2-cyanoethyl, tetrahydropyranyloxy-lower alkyl, typically 4-(tetrahydropyranyl)-oxymethyl, morpholino-lower alkyl, typically 2-(morpholino)ethyl, phenyl, lower alkylphenyl, typically 4-methylphenyl, lower alkoxyphenyl, typically 4-methoxyphenyl, imidazolyl-lower alkoxyphenyl, typically 4-[2-(imidazol-1-yl)ethyl)oyxphenyl, carboxyphenyl, typically 4-carboxyphenyl, lower alkoxycarbonylphenyl, typically 4-ethoxycarbonylphenyl or 4-methoxyphenyl, halogen-lower alkylphenyl, typically 4-chloromethylphenyl, pyrrolidinophenyl, typically 4-pyrrolidinophenyl, imidazol-1-ylphenyl, typically 4-(imidazolyl-1-yl)phenyl, piperazinophenyl, typically 4-piperazinophenyl, (4-lower alkylpiperazino)phenyl, typically 4-(4-methylpiperazino)phenyl, morpholinophenyl, typically 4-morpholinophenyl, pyrrolidino-lower alkylphenyl, typically 4-pyrrolidinomethylphenyl, imidazol-1-yl-lower alkylphenyl, typically 4-(imidazolyl-1-ylmethyl)phenyl, piperazino-lower alkylphenyl, typically 4-piperazinomethylphenyl, (4-lower alkylpiperazinomethyl)-phenyl, typically 4-(4-methylpiperazinomethyl)phenyl, morpholino-lower alkylphenyl, typically 4-morpholinomethylphenyl, piperazinocarbonylphenyl, typically 4-piperazinocarbonylphenyl, or (4-lower alkyl-piperazino) phenyl, typically 4-(4-methylpiperazino)phenyl.

Preferred acyl radicals $Ac^1$ are acyl radicals of a carboxylic acid which are characterised by the subformula $R^o$—CO—, wherein $R^o$ has one of the above general and preferred meanings of the hydrocarbyl radical $R^o$. Especially preferred radicals $R^o$ here are lower alkyl especially methyl or ethyl, amino-lower alkyl wherein the amino group is unprotected or protected by a conventional amino protecting group, especially by lower alkoxycarbonyl, typically tert-lower alkoxycarbonyl, for example tert-butoxycarbonyl, e.g. aminomethyl, R,S-, R-, or preferably S-1-aminoethyl, tert-butoxycarbonylaminomethyl or R,S-, R-, or preferably S-1-(tert-butoxycarbonylamino)ethyl, carboxy-lower alkyl typically 2-carboxyethyl, lower alkoxycarbonyl-lower alkyl typically 2-(tert-butoxycarbonyl)ethyl, tetrahydropyranyloxy-lower alkyl typically 4-(tetrahydropyranyl)oxymethyl, phenyl, imidazolyl-lower alkoxyphenyl, typically 4-[2-(imidazol-1-yl)ethyl]oyxphenyl, carboxyphenyl, typically 4-carboxyphenyl, lower alkoxycarbonylphenyl, typically 4-ethoxycarbonylphenyl, halogen-lower alkylphenyl, typically 4-chloromethylphenyl, imidazol-1-ylphenyl, typically 4-(imidazolyl-1-yl)phenyl, pyrrolidino-lower alkylphenyl, typically 4-pyrrolidinomethylphenyl, piperazino-lower alkylphenyl, typically 4-piperazinomethylphenyl, (4-lower alkylpiperazinomethyl)phenyl, typically 4-(4-methylpiperazinomethyl)phenyl, morpholino-lower alkylphenyl, typically 4-morpholinomethylphenyl, piperazinocarbonylphenyl, typically 4-piperazinocarbonylphenyl, or (4-lower alkylpiperazino)phenyl, typically 4-(4-methylpiperazino)phenyl.

A further preferred Acyl $Ac^1$ is derived from monoesters of carbonic acid and is characterised by the subformula $R^o$—O—CO—. The lower alkyl radicals, especially tert-butyl, are especially preferred hydrocarbyl radicals $R^o$ in these derivatives.

Another preferred Acyl $Ac^1$ is derived from amides of carbonic acid (or also thiocarbonic acid) and is characterised by the formula $R^oHN$—C(=W)— or $R^oR^oN$—C(=W)—, wherein the radicals $R^o$ are, independently of one another, as defined above and W is sulfur and especially oxygen. In particular, compounds are preferred wherein $Ac^1$ is a radical of formula $R^oHN$—C(=W)—, wherein W is oxygen and $R^o$ has one of the following preferred meanings: morpholino-lower alkyl typically 2-morpholinoethyl, phenyl, lower alkoxyphenyl, typically 4-methoxyphenyl or 4-ethoxyphenyl, carboxyphenyl, typically 4-carboxyphenyl, or lower alkoxycarbonylphenyl, typically 4-ethoxycarbonylphenyl.

A preferred acyl $Ac^2$ of subformula $R^o$—$SO_2$—, wherein $R^o$ is a hydrocarbyl as defined in the above general and specific meanings, is lower alkylphenylsulfonyl, typically 4-toluenesulfonyl.

If p is 0, the nitrogen atom bonding $R_3$ is uncharged. If p is 1, then $R_4$ must also be present, and the nitrogen atom bonding $R_3$ and $R_4$ (quaternary nitrogen) is then positively charged.

The definitions for an aliphatic, carbocyclic, or carbocyclic-aliphatic radical with up to 29 carbon atoms each, or for a heterocyclic or heterocyclic-aliphatic radical with up to 20 carbon atoms each and up to 9 heteroatoms each, or acyl with up to 30 carbon atoms each, preferably match the definitions given for the corresponding radicals $R_3$ and $R_4$. Especially preferred is $R_5$ lower alkyl, especially methyl, or most especially hydrogen.

Z is especially lower alkyl, most especially methyl or hydrogen.

If the two bonds indicated by wavy lines are missing in ring A, then no double bonds (tetra-hydrogenated derivatives) are present between the carbon atoms characterised in formula I by the numbers 1, 2, 3, and 4, but only single bonds, whereas ring B is aromatic (double bonds between the carbon atoms characterised in formula I by 8 and 9 and those characterised by 10 and 11). If the two bonds indicated by wavy lines are missing in ring B, then no double bonds (tetra-hydrogenated derivatives) are present between the carbon atoms characterised in formula I by the numbers 8, 9, 10, and 11, but only single bonds, whereas ring A is aromatic (double bonds between the carbon atoms characterised in formula I by 1 and 2 and those characterised by 3 and 4). If the total of four bonds indicated by wavy lines are missing in rings A and B, and are replaced by a total of 8 hydrogen atoms, then no double bonds (octa-hydrogenated derivatives) are present between the carbon atoms numbered 1, 2, 3, 4, 8, 9, 10, and 11 in formula I, but only single bonds.

By their nature, the compounds of the invention may also be present in the form of pharmaceutically, i.e. physiologically, acceptable salts, provided they contain salt-forming groups. For isolation and purification, pharmaceutically unacceptable salts may also be used. For therapeutic use, only pharmaceutically acceptable salts are used, and these salts are preferred.

Thus, compounds of formula I having free acid groups, for example a free sulfo, phosphoryl or carboxyl group, may exist as a salt, preferably as a physiologically acceptable salt with a salt-forming basic component. These may be primarily metal or ammonium salts, such as alkali metal or alkaline earth metal salts, for example sodium, potassium, magnesium or calcium salts, or ammonium salts with ammonia or suitable organic amines, especially tertiary monoamines and heterocyclic bases, for example triethylamine, tri-(2-hydroxyethyl)-amine, N-ethylpiperidine or N,N'-dimethylpiperazine.

Compounds of the invention having a basic character may also exist as addition salts, especially as acid addition salts with inorganic and organic acids, but also as quaternary salts. Thus, for example, compounds which have a basic group, such as an amino group, as a substituent may form acid addition salts with common acids. Suitable acids are, for example, hydrohalic acids, e.g. hydrochloric and hydrobromic acid, sulfuric acid, phosphoric acid, nitric acid or perchloric acid, or aliphatic, alicyclic, aromatic or heterocyclic carboxylic or sulfonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic, p-aminosalicylic acid, pamoic acid, methanesulfonic, ethanesulfonic, hydroxyethanesulfonic, ethylenedisulfonic, halobenzenesulfonic, toluenesulfonic, naphthalenesulfonic acids or sulfanilic acid, and also methionine, tryptophan, lysine or arginine, as well as ascorbic acid.

In view of the close relationship between the compounds (especially of formula I) in free form and in the form of their salts, including those salts that can be used as intermediates, for example in the purification or identification of the novel compounds, and of their solvates, any reference hereinbefore and hereinafter to the free compounds is to be understood as referring also to the corresponding salts, and the solvates thereof, for example hydrates, as appropriate and expedient.

The compounds of formula A, B, C, D, I, II, III, IV, V or VI especially those wherein $R_5$ is hydrogen, possess valuable pharmacological properties.

In the case of the groups of radicals or compounds mentioned hereinbefore and hereinafter, general definitions may, insofar as appropriate and expedient, be replaced by the more specific definitions stated hereinbefore and hereinafter.

Preference is given to a compounds of formula I, II, III, IV, V, VI wherein $R_1$ and $R_2$ independently of each other are lower alkyl, lower alkyl substituted by halogen, $C_6$-$C_{14}$aryl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl)amino, cyano, mercapto, lower alkylthio, carboxy, lower alkoxycarbonyl, carbamoyl, N-lower alkylcarbamoyl, N,N-di-lower alkylcarbamoyl, sulfo, lower alkanesulfonyl, lower alkoxysulfonyl, aminosulfonyl, N-lower alkylaminosulfonyl or N,N-di-lower alkylaminosulfonyl; halogen; lower alkoxy; $C_6$-$C_{14}$aryloxy; $C_6$-$C_{14}$aryl-lower alkoxy; lower alkanoyloxy; $C_6$-$C_{14}$arylcarbonyloxy; amino monosubstituted or disubstituted by lower alkyl, $C_6$-$C_{14}$aryl, $C_6$-$C_{14}$aryl-lower alkyl, lower alkanoyl or $C_6$-$C_{12}$arylcarbonyl; cyano; nitro; mercapto; lower alkylthio; $C_6$-$C_{14}$arylthio; $C_6$-$C_{14}$aryl-lower alkylthio; lower alkanoylthio; $C_6$-$C_{14}$aryl-lower alkanoylthio; carboxy; lower alkoxycarbonyl, $C_6$-$C_{14}$aryl-lower alkoxycarbonyl; $C_6$-$C_{14}$aryloxycarbonyl; carbamoyl; carbamoyl N-mono- or N,N-disubstituted by lower alkyl, $C_6$-$C_{14}$aryl or $C_6$-$C_{14}$aryl-lower alkyl; sulfo; $C_6$-$C_{14}$arylsulfonyl; $C_6$-$C_{14}$aryl-lower alkanesulfonyl; lower alkanesulfonyl; or aminosulfonyl N-mono- or N,N-disubstituted by lower alkyl, $C_6$-$C_{14}$aryl or $C_6$-$C_{14}$aryl-lower alkyl, wherein $C_6$-$C_{14}$aryl is an aryl radical with 6 to 12 carbon atoms in the ring system, which may be unsubstituted or substituted by halogen, phenyl or naphthyl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl)amino, cyano, mercapto, lower alkylthio, carboxy, lower alkoxycarbonyl, carbamoyl, N-lower alkylcarbamoyl, N,N-di-lower alkylcarbamoyl, sulfo, lower alkanesulfonyl, lower alkoxysulfonyl, aminosulfonyl, N-lower alkylaminosulfonyl or N,N-di-lower alkylaminosulfonyl;

n and m are independently of each other 0 or 1 or 2, preferably 0;

$R_3$, $R_4$, $R_8$, $R_{10}$ are independently of each other hydrogen, lower alkyl, lower alkenyl or lower alkadienyl, which are each unsubstituted or monosubstituted or polysubstituted, preferably monosubstituted or disubstituted by a substituent independently selected from lower alkyl; hydroxy; lower alkoxy, which may be unsubstituted or mono-, di-, or trisubstituted by (i) heterocyclyl with 4 to 12 ring atoms, which may be unsaturated, wholly saturated, or partly saturated, is monocyclic or bicyclic and may contain up to three heteroatoms selected from nitrogen, oxygen and sulfur, and is most especially pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl, (ii) by halogen, (iii) by hydroxy or (iv) by lower alkoxy; phenoxy;

phenyl-lower alkoxy; heterocyclyloxy, wherein heterocyclyl is pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl, such as especially 2- or 4-tetrahydropyranyloxy; lower alkanoyloxy; carboxy; lower alkoxycarbonyl; phenyl-lower alkoxycarbonyl; mercapto; lower alkylthio; phenylthio; halogen; halogen-lower alkyl; oxo (except in the 1-position, because otherwise acyl); azido; nitro; cyano; amino; mono-lower alkylamino; di-lower alkylamino; pyrrolidino; imidazol-1-yl; piperidino; piperazino; 4-lower alkylpiperazino; morpholino; thiomorpholino; diphenylamino or dibenzylamino unsubstituted or substituted in the phenyl part by lower alkyl, lower alkoxy, halogen and/or nitro; lower alkoxycarbonylamino; phenyl-lower alkoxycarbonylamino unsubstituted or substituted in the phenyl part by lower alkyl or lower alkoxy; fluorenyl-methoxycarbonylamino; amino-lower alkyl; monosubstituted or disubstituted amino-lower alkyl, wherein the amino substituent is selected from lower alkyl, hydroxy-lower alkyl, $C_3$-$C_8$cycloalkyl, amino-lower alkyl, N-mono- or N,N-di(-lower alkyl)amino-lower alkyl, amino, N-mono- or N,N-di-lower alkylamino and N-mono- or N,N-di-(hydroxy-lower alkyl)amino; pyrrolidino-lower alkyl; piperidino-lower alkyl; piperazino-lower alkyl; 4-lower alkylpiperazino-lower alkyl; imidazol-1-yl-lower alkyl; morpholino-lower alkyl; thiomorpholino-lower alkyl; S-oxo-thiomorpholino-lower alkyl; S,S-dioxothiomorpholino-lower alkyl; lower alkylendioxy; sulfamoyl; sulfo; carbamoyl; ureido; guanidino; cyano; aminocarbonyl (carbamoyl) and aminocarbonyloxy, which are substituted by one or two radicals on the nitrogen, wherein the amino substituents are selected independently of one another from the group comprising lower alkyl hydroxy-lower alkyl $C_3$-$C_8$cycloalkyl, amino-lower alkyl N-mono- or N,N-di(-lower alkyl)amino-lower alkyl amino, N-mono- or N,N-di-lower alkylamino and N-mono- or N,N-di-(hydroxy-lower alkyl)amino; pyrrolidinocarbonyl; piperidinocarbonyl; piperazinocarbonyl; 4-lower alkylpiperazinocarbonyl; imidazolinocarbonyl; morpholinocarbonyl; thiomorpholinocarbonyl; S-oxo-thiomorpholinocarbonyl; and S,S-dioxothiomorpholino; phenyl, naphthyl, phenyl-lower alkyl or phenyl-lower alkenyl with a terminal phenyl radical, which is unsubstituted or monosubstituted or disubstituted by the radicals named above as substituents of lower alkyl lower alkenyl or lower alkadienyl; or heterocyclyl-lower alkyl wherein heterocyclyl is pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl, which in each case are unsubstituted or monosubstituted or disubstituted by the radicals named above as substituents of lower alkyl lower alkenyl, or lower alkadienyl;

or acyl of the subformula Y—C(=W)—, wherein W is oxygen and Y is hydrogen, R°, R°—O—, R°HN—, or R°R°N— (wherein the radicals R° may be the same or different), or acyl of the subformula R°—SO$_2$—, whereby $R_4$ may also be absent for the compound of formula II;

or $R_4$ is absent for compounds of formula II, hydrogen or $CH_3$ for compounds of formula I, and $R_3$ is acyl of the subformula Y—C(=W)—, wherein W is oxygen and Y is hydrogen, R°, R°—O—, R°HN—, or R°R°N— (wherein the radicals R° may be the same or different), or is acyl of the subformula R°—SO$_2$—, wherein $R^0$ in the said radicals has the following meanings: substituted or unsubstituted lower alkyl, especially methyl or ethyl, amino-lower alkyl hydroxy-lower alkyl, wherein the amino group is unprotected or is protected by a conventional amino protecting group—especially by lower alkoxycarbonyl, typically tert-lower alkoxycarbonyl, for example tert-butoxycarbonyl—e.g. aminomethyl, R,S-, R- or preferably S-1-aminoethyl, tert-butoxycarbonylaminomethyl or R,S-, R-, or preferably S-1-(tert-butoxycarbonylamino)ethyl, carboxy-lower alkyl, typically 2-carboxyethyl, lower alkoxycarbonyl-lower alkyl, typically 2-(tert-butoxycarbonyl)ethyl, cyano-lower alkyl, typically 2-cyanoethyl, tetrahydropyranyloxy-lower alkyl, typically 4-(tetrahydropyranyl)oxymethyl, morpholino-lower alkyl, typically 2-(morpholino)ethyl, phenyl, lower alkylphenyl, typically 4-methylphenyl, lower alkoxyphenyl, typically 4-methoxyphenyl, imidazolyl-lower alkoxyphenyl, typically 4-[2-(imidazol-1-yl)ethyl)oxyphenyl, carboxyphenyl, typically 4-carboxyphenyl, lower alkoxycarbonylphenyl, typically 4-ethoxycarbonylphenyl or 4-methoxyphenyl, halogen-lower alkylphenyl, typically 4-chloromethylphenyl, pyrrolidinophenyl, typically 4-pyrrolidinophenyl, imidazol-1-ylphenyl, typically 4-(imidazolyl-1-yl)phenyl, piperazinophenyl, typically 4-piperazinophenyl, (4-lower alkylpiperazino)phenyl, typically 4-(4-methylpiperazino)phenyl, morpholinophenyl, typically 4-morpholinophenyl, pyrrolidino-lower alkylphenyl, typically 4-pyrrolidinomethylphenyl, imidazol-1-yl-lower alkylphenyl, typically 4-(imidazolyl-1-ylmethyl)phenyl, piperazino-lower alkylphenyl, typically 4-piperazinomethylphenyl, (4-lower alkylpiperazinomethyl)-phenyl, typically 4-(4-methylpiperazinomethyl)phenyl, morpholino-lower alkylphenyl, typically 4-morpholinomethylphenyl, piperazinocarbonylphenyl, typically 4-piperazinocarbonylphenyl, or (4-lower alkylpiperazino)phenyl, typically 4-(4-methylpiperazino)phenyl.

p is 0 if $R_4$ is absent, or is 1 if $R_3$ and $R_4$ are both present and in each case are one of the aforementioned radicals (for compounds of formula II);

$R_5$ is hydrogen or lower alkyl, especially hydrogen,

X stands for 2 hydrogen atoms, for O, or for 1 hydrogen atom and hydroxy; or for 1 hydrogen atom and lower alkoxy;

Z is hydrogen or especially lower alkyl, most especially methyl;

and for compounds for formula II, either the two bonds characterised by wavy lines are preferably absent in ring A and replaced by 4 hydrogen atoms, and the two wavy lines in ring B each, together with the respective parallel bond, signify a double bond;

or also the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present.

Particular preference is given to a compound of formula I wherein;

m and n are each 0;

$R_3$ and $R_4$ are independently of each other hydrogen, lower alkyl unsubstituted or mono- or disubstituted, especially monosubstituted, by radicals selected independently of one another from carboxy; lower alkoxycarbonyl; and cyano;

or $R_4$ is hydrogen or —$CH_3$, and $R_3$ is as defined above or preferably $R_3$ is, acyl of the subformula $R^°$—CO, wherein $R^°$ is lower alkyl; amino-lower alkyl wherein the amino group is present in unprotected form or is protected by lower alkoxycarbonyl; tetrahydropyranyloxy-lower alkyl; phenyl; imidazolyl-lower alkoxyphenyl; carboxyphenyl; lower alkoxycarbonylphenyl; halogen-lower alkylphenyl; imidazol-1-ylphenyl; pyrrolidino-lower alkylphenyl; piperazino-lower alkylphenyl; (4-lower alkylpiperazinomethyl)phenyl; morpholino-lower alkylphenyl; piperazinocarbonylphenyl; or (4-lower alkylpiperazino)phenyl;

or is acyl of the subformula $R^°$—O—CO—, wherein $R^°$ is lower alkyl;

or is acyl of the subformula $R^°HN$—C(=W)—, wherein W is oxygen and $R^°$ has the following meanings: morpholino-lower alkyl phenyl, lower alkoxyphenyl, carboxyphenyl, or lower alkoxycarbonylphenyl;

or $R_3$ is lower alkylphenylsulfonyl, typically 4-toluenesulfonyl, wherein further specific examples of preferred $R_3$ groups are described below for the preferred compounds of formula II, $R_5$ is hydrogen or lower alkyl especially hydrogen, X stands for 2 hydrogen atoms or for O;

Z is methyl or hydrogen;

or a salt thereof, if at least one salt-forming group is present.

Particular preference is given to a compound of formula II wherein m and n are each 0;

$R_3$ and $R_4$ are independently of each other: hydrogen, lower alkyl unsubstituted or mono- or disubstituted, especially monosubstituted, by radicals selected independently of one another from carboxy; lower alkoxycarbonyl; and cyano; whereby $R_4$ may also be absent;

or $R_4$ is absent, and $R_3$ is acyl from the subformula $R^°$—CO, wherein $R^°$ is lower alkyl especially methyl or ethyl; amino-lower alkyl wherein the amino group is unprotected or protected by lower alkoxycarbonyl, typically tert-lower alkoxycarbonyl, for example tert-butoxycarbonyl, e.g. aminomethyl, R,S-, R-, or preferably S-1-aminoethyl, tert-butoxycarbonylaminomethyl or R,S-, R-, or preferably S-1-(tert-butoxycarbonylamino)ethyl; tetrahydropyranyloxy-lower alkyl typically 4-(tetrahydropyranyl)oxymethyl; phenyl; imidazolyl-lower alkoxyphenyl, typically 4-[2-(imidazol-1-yl)ethyl)oyxphenyl; carboxyphenyl, typically 4-carboxyphenyl; lower alkoxycarbonylphenyl, typically 4-methoxy- or 4-ethoxycarbonylphenyl; halogen-lower alkylphenyl, typically 4-chloromethylphenyl; imidazol-1-ylphenyl, typically 4-(imidazolyl-1-yl)-phenyl; pyrrolidino-lower alkylphenyl, typically 4-pyrrolidinomethylphenyl; piperazino-lower alkylphenyl, typically 4-piperazinomethylphenyl; (4-lower alkylpiperazinomethyl)phenyl, typically 4-(4-methylpiperazinomethyl) phenyl; morpholino-lower alkylphenyl, typically 4-morpholinomethylphenyl; piperazinocarbonylphenyl, typically 4-piperazinocarbonylphenyl; or (4-lower alkylpiperazino) phenyl, typically 4-(4-methylpiperazino)phenyl;

or is acyl of the subformula $R^°$—O—CO—, wherein $R^°$ is lower alkyl;

or is acyl of the subformula $R^°HN$—C(=W)—, wherein W is oxygen and $R^°$ has the following preferred meanings: morpholino-lower alkyl typically 2-morpholinoethyl, phenyl, lower alkoxyphenyl, typically 4-methoxyphenyl or 4-ethoxyphenyl, carboxyphenyl, typically 4-carboxyphenyl, or lower alkoxycarbonylphenyl, typically 4-ethoxycarbonylphenyl;

or is lower alkylphenylsulfonyl, typically 4-toluenesulfonyl;

p is 0 if $R_4$ is absent, or is 1 if $R_3$ and $R_4$ are both present and in each case are one of the aforementioned radicals;

$R_5$ is hydrogen or lower alkyl especially hydrogen,

X stands for 2 hydrogen atoms or for O;

Z is methyl or hydrogen;

and either the two bonds characterised by wavy lines are preferably absent in ring A and replaced by 4 hydrogen atoms, and the two wavy lines in ring B each, together with the respective parallel bond, signify a double bond;

or also the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present.

Most especially preferred compounds of formula II are selected from;

8,9,10,11-Tetrahydrostaurosporine;

N-[4-(4-methylpiperaziN-1-ylmethyl)benzoyl]-1,2,3,4-tetrahydrostaurosporine;

N-(4-chloromethylbenzoyl)-1,2,3,4-tetrahydrostaurosporine;

N-(4-(pyrrolidin-1-ylmethyl)benzoyl)-1,2,3,4-tetrahydrostaurosporine;

N-(4-(morpholin-4-ylmethyl)benzoyl)-1,2,3,4-tetrahydrostaurosporine;

N-(4-(piperazin-1-ylmethyl)benzoyl)-1,2,3,4-tetrahydrostaurosporine;

N-ethyl-1,2,3,4-tetrahydrostaurosporine;

N-tosyl-1,2,3,4-tetrahydrostaurosporine;

N-trifluoroacetyl-1,2,3,4-tetrahydrostaurosporine;

N-[4-(2-imidazol-1-yl-ethoxy)benzoyl]-1,2,3,4-tetrahydrostaurosporine;

N-methoxycarbonyl methyl-1,2,3,4-tetrahydrostaurosporine;

N-carboxymethyl-1,2,3,4-tetrahydrostaurosporine;

N-terephthaloylmethyl ester-1,2,3,4-tetrahydrostaurosporine;

N-terephthaloyl-1,2,3,4-tetrahydrostaurosporine;

N-(4-ethylpiperazinylcarbonylbenzoyl)-1,2,3,4-tetrahydrostaurosporine;
N-(2-cyanoethyl)-1,2,3,4-tetrahydrostaurosporine;
N-benzoyl-1,2,3,4-tetrahydrostaurosporine;
N,N-dimethyl-1,2,3,4-tetrahydrostaurosporinium iodide;
N-BOC-glycyl-1,2,3,4-tetrahydrostaurosporine;
N-glycyl-1,2,3,4-tetrahydrostaurosporine;
N-(3-(tert-butoxycarbonyl)propyl)-1,2,3,4-tetrahydrostaurosporine;
N-(3-carboxypropyl)-1,2,3,4-tetrahydrostaurosporine;
N-(4-imidazol-1-yl)benzoyl]-1,2,3,4-tetrahydrostaurosporine;
N-[(tetrahydro-2h-pyran-4-yloxy)acetyl]-1,2,3,4-tetrahydrostaurosporine;
N-BOC-l-alanyl-1,2,3,4-tetrahydrostaurosporine;
N-l-alanyl-1,2,3,4-tetrahydrostaurosporine hydrochloride;
N-methyl-1,2,3,4-tetrahydro-6-methylstaurosporine;
N-(4-carboxyphenylaminocarbonyl)-1,2,3,4-tetrahydrostaurosporine;
N-(4-ethylphenylaminocarbonyl)-1,2,3,4-tetrahydrostaurosporine;
N—(N-phenylaminocarbonyl)-1,2,3,4-tetrahydrostaurosporine;
N—(N-[2-(1-morpholino)ethyl]aminocarbonyl)-1,2,3,4-tetrahydrostaurosporine;
N—(N-[4-methoxyphenyl]aminocarbonyl)-1,2,3,4-tetrahydrostaurosporine;
1,2,3,4-tetrahydro-6-methylstaurosporine;
N-BOC-1,2,3,4-tetrahydrostaurosporine;
N-BOC-1,2,3,4-tetrahydro-6-methylstaurosporine;
N-BOC-1,2,3,4-tetrahydro-6-methyl-7-oxo-staurosporine;
1,2,3,4,8,9,10,11-octahydrostaurosporine;
or a pharmaceutically acceptable salt thereof, if at least one salt-forming group is present.

Most especially preferred is the compound of formula I designated 1,2,3,4-tetrahydrostaurosporine, or a (particularly pharmaceutically acceptable) salt thereof (here, m und n in formula I are 0, $R_3$ is hydrogen, $R_4$ is absent, provided no salt is present (p=0), or is hydrogen if a salt is present (p=1), $R_5$ is hydrogen, the two bonds represented by wavy lines are absent in Ring A and are replaced by a total of 4 hydrogen atoms and the two bonds represented by wavy lines in Ring B are in each case a double bond together with the parallel bonds, X stands for 2 hydrogen atoms, and Z is methyl).

Most especially preferred are the compounds of formula A wherein;
A) X=O; $R_1$, $R_2$, $R_5$=H; Q=—$(CH_2)_2$—O—CH($CH_2$)OH—$(CH_2)_2$—
B) X=O; $R_1$, $R_2$, $R_5$=H; Q=—$(CH_2)_2$—O—CH($CH_2$N($CH_3)_2$)—$(CH_2)_2$—
C) X=2 hydrogen atoms; $R_1$, $R_2$, $R_5$=H; Q=

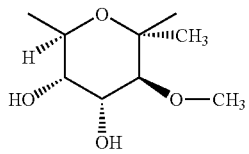

Most especially preferred are the compounds of formula I wherein;
A) X=2 hydrogen atoms; $R_1$, $R_2$, $R_3$, $R_5$=H; $R_4$=$CH_3$; Z=$CH_3$ (staurosporine)
B) X=1 hydrogen and 1 hydroxy atoms in (R) or (S) isomeric form; $R_1$, $R_2$, $R_3$, $R_5$=H; $R_4$=$CH_3$; Z=$CH_3$ (UCN-01 and UCN-02)
C) X=2 hydrogen atoms; $R_1$, $R_2$, $R_5$=H; $R_4$=$CH_3$; $R_3$, = benzoyl; Z=$CH_3$ (CGP41251 or PKC412 or MIDOSTAURIN)
D) X=O; $R_1$, $R_2$, $R_5$=H; $R_3$, =$CH_3$; $R_4$=ethyloxycarbonyl; Z=$CH_3$ (NA 382; CAS=143086-33-3)
E) X=1 hydrogen and 1 hydroxy atom; $R_1$, $R_2$, $R_5$=H; $R_3$=$CH_3$; Z=$CH_3$; and $R_4$ is selected from —$(CH_2)_2$OH; —$CH_2CH(OH)CH_2OH$; —$CO(CH_2)_2CO_2Na$; —$(CH_2)_3CO_2H$; —$COCH_2N(CH_3)_2$;

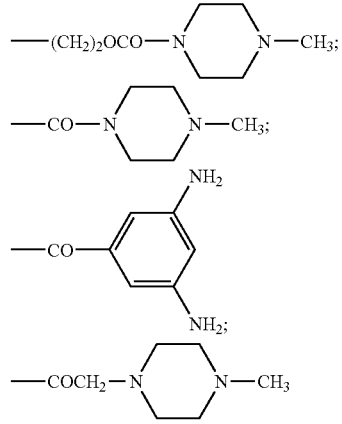

F) X=2 hydrogen atoms; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-methyl-2-(tetrahydropyran-4-yloxy)-propionyl]; N-[0-(tetrahydropyran-4-yl)-L-lactoyl]; N-[0-(tetrahydropyran-4-yl)-D-lactoyl]; N-[2-(tetrahydro-pyran-4-yloxy)-acetyl)]
G) X=O; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-(tetrahydro-pyran-4-yloxy)-acetyl)]
H) X=1 hydrogen and 1 hydroxy atom; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-(tetrahydro-pyran-4-yloxy)-acetyl)]

The abbreviation "CAS" means the CHEMICAL ABSTRACTS registry number.

The most preferred compounds of formula I e.g. MIDOSTAURIN [International Nonproprietary Name] are covered and have been specifically described by the European patent No. 0 296 110 published on Dec. 21, 1988, as well as in U.S. Pat. No. 5,093,330 published on Mar. 3, 1992, and Japanese Patent No. 2 708 047. Other preferred compounds are covered and described by the patent applications WO 95/32974 and WO 95/32976 both published on Dec. 7, 1995. All the compounds described in these documents are incorporated into the present application by reference.

Most especially preferred are the compounds of formula III wherein;
A) X=2 hydrogen atoms; $R_1$, $R_2$, $R_5$=H; $R_6$=$CH_3$; $R_7$=methyloxycarbonyl; Z=H (2-methyl K252a)
B) X=2 hydrogen atoms; $R_1$, $R_2$, $R_5$, $R_6$=H; $R_7$=methyloxycarbonyl; Z=H (K-252a)
C) X=2 hydrogen atoms; $R_1$, $R_2$, $R_5$, $R_6$=H; $R_7$=methyloxycarbonyl; Z=$CH_3$ (KT-5720)

Most especially preferred are the compounds of formula IV wherein;
A) X=O; $R_1$, $R_2$, $R_5$=H; $R_9$=$CH_2$—$NMe_2$; $R_8$=$CH_3$; m'=n'=2

B) X=O; $R_1$, $R_2$, $R_5$=H; $R_9$=$CH_2$—$NH_2$; $R_8$=$CH_3$; m'=2; n'=1 (Ro-31-8425; CAS=151342-35-7)

Most especially preferred are the compounds of formula V wherein;
A) X=O; $R_1$, $R_2$, $R_5$=H; $R_8$=$CH_3$; $R_{10}$=—$(CH_2)_3$—$NH_2$; (Ro-31-7549; CAS=138516-31)
B) X=O; $R_1$, $R_2$, $R_5$=H; $R_8$=$CH_3$; $R_{10}$=—$(CH_2)_3$—S—(C=NH)—$NH_2$; (Ro-31-8220; CAS=125314-64-9))
C) X=O; $R_1$, $R_2$, $R_5$=H; $R_8$=$CH_3$; $R_{10}$=—$CH_3$;

Most especially preferred are the compounds of formula VI wherein;
A) X=2 hydrogen atoms; $R_1$, $R_2$, $R_5$=H; $R_4$=$CH_3$; Z=$CH_3$; $R_3$ selected from methyl or $(C_1-C_{10})$alkyl, arylmethyl, $C_6H_2CH_2$—

STAUROSPORINE DERIVATIVES and their manufacturing process have been specifically described in many prior documents, well known by the man skilled in the art.

Compounds of formula A, B, C, D and their manufacturing process have for instance, been described in the European patents No. 0 657 458 published on Jun. 14, 1995, in the European patents No. 0 624 586 published on Nov. 17, 1994, in the European patents No. 0 470 490 published on Feb. 12, 1992, in the European patents No. 0 328 026 published on Aug. 16, 1989, in the European patents No. 0 384 349 published on Aug. 29, 1990, as well as in many publications such as Barry M. Trost* and Weiping Tang Org. Lett., 3(21), 3409-3411.

Compounds of formula I and their manufacturing processes have specifically been described in the European patents No. 0 296 110 published on Dec. 21, 1988, as well as in U.S. Pat. No. 5,093,330 published on Mar. 3, 1992, and Japanese Patent No. 2 708 047. Compounds of formula I having a tetrahydropyran-4-yl)-lactoyl substitution on $R_4$ have been described in the European patent No. 0 624 590 published on Nov. 17, 1994. Other compounds have been described in the European patent No. 0 575 955 published Dec. 29, 1993, European patent No. 0 238 011 published on Sep. 23, 1987 (UCN-O1), International patent application EP98/04141 published as WO99/02532 on Jul. 3, 1998.

Compounds of formula II and their manufacturing processes have specifically been described in the European patents No. 0 296 110 published on Dec. 21, 1988, as well as in U.S. Pat. No. 5,093,330 published on Mar. 3, 1992, and Japanese Patent No. 2 708 047.

Compounds of formula III and their manufacturing processes have specifically been described in the patent applications claiming the priority of the U.S. patent application Ser. No. 07/920,102 filed on Jul. 24, 1992. (i.e European patents No. 0 768 312 published on Apr. 16, 1997, No. 1 002 534 published May 24, 2000, No. 0 651 754 published on May 10, 1995).

Compounds of formula IV and their manufacturing processes have specifically been described in the patent applications claiming the priority of the British patent applications GB 9309602 and GB 9403249 respectively filed on May 10, 1993, and on Feb. 21, 1994. (i.e European patents No. 0 624 586 published on Nov. 17, 1994, No. 1 002 534 published May 24, 2000, No. 0 651 754 published on May 10, 1995).

Compounds of formula V and their manufacturing processes have specifically been described in the patent applications claiming the priority of the British patent applications GB 8803048, GB 8827565, GB 8904161 and GB 8928210 respectively filed on Feb. 10, 1988, Nov. 25, 1988, Feb. 23, 1989 and Dec. 13, 1989. (i.e European patents No. 0 328 026 published on Aug. 16, 1989, and No. 0 384 349 published Aug. 29, 1990).

Compounds of formula VI and their manufacturing processes have specifically been described in the patent applications claiming the priority of the U.S. patent application Ser. Nos. 07/777,395 (Con), filed on Oct. 10, 1991 (i.e International patent application WO 93/07153 published on Apr. 15, 1993).

In each case where citations of patent applications or scientific publications are given in particular for the STAUROSPORINE DERIVATIVE compounds, the subject-matter of the final products, the pharmaceutical preparations and the claims are hereby incorporated into the present application by reference to these publications.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The preferred STAUROSPORINE DERIVATIVE according to the invention is N-[(9S,10R,11R,13R)-2,3,10,11,12, 13-hexahydro-1 0-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide of the formula (VII):

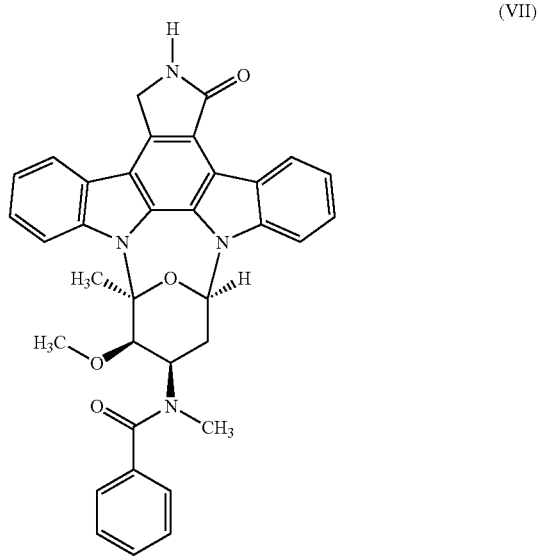

(VII)

or a salt thereof, (hereinafter: "Compound of formula VII or MIDOSTAURIN").

Compound of formula VII is also known as MIDOSTAURIN [International Nonproprietary Name] or PKC412.

MIDOSTAURIN is a derivative of the naturally occurring alkaloid staurosporine, and has been specifically described in the European patent No. 0 296 110 published on Dec. 21, 1988, as well as in U.S. Pat. No. 5,093,330 published on Mar. 3, 1992, and Japanese Patent No. 2 708 047.

Further the invention provides the use of a compound of formula I (or pharmaceutically acceptable salt or prodrug ester thereof) for the preparation of a medicament for use in the treatment of a proliferative disease.

In a further aspect the invention provides use of a compound of formula I (or pharmaceutically acceptable salt or prodrug ester thereof) for the treatment of a proliferative disease, especially a sarcoma, more especially aRMS.

In yet further aspect the invention provides a compound of formula I (or pharmaceutically acceptable salt or prodrug ester thereof) as active ingredient for use in the treatment of a proliferative disease, especially a sarcoma, more especially aRMS.

In still yet further aspect the invention provides a package comprising a compound of formula I (or pharmaceutically acceptable salt or prodrug ester thereof) together with instructions for the use for the treatment of a proliferative disease, especially a sarcoma, more especially aRMS.

The term "delay of progression" as used herein means administration of the composition to patients being in an early phase of the proliferative disease to be treated.

The term "solid tumor disease" as used herein comprises, but is not restricted to glioma, thyroid cancer, breast cancer, ovarian cancer, cancer of the colon and generally the GI tract, cervix cancer, lung cancer, in particular small-cell lung cancer, and non-small-cell lung cancer, head and neck cancer, bladder cancer, cancer of the prostate, or a sarcoma such as Kaposi's sarcoma or Alveolar Rhabdomyosarcoma. In one preferred embodiment of the invention, the tumor disease to be treated is Alveolar Rhabdomyosarcoma, glioma, cancer of the prostate or thyroid cancer. The present composition inhibits the growth of solid tumors, but also liquid tumors. Furthermore, depending on the tumor type and the particular composition used, a decrease of the tumor volume can be obtained. The composition disclosed herein is also suited to prevent the metastatic spread of tumors and the growth or development of micrometastases.

The nature of proliferative diseases like solid tumor diseases is multifactorial. Under certain circumstances, drugs with different mechanisms of action may be combined. However, just considering any combination of drugs having different mode of action does not necessarily lead to combinations with advantageous effects.

In one embodiment, the composition of the invention is administered in combination with radiation. Combination refers to administration of an amount of a compound of formula I in combination with administration of an amount of ionizing radiation such that there is a synergistic effect which would not be obtained if a compound of formula I is administered without separate, simultaneous or sequential administration of ionizing radiation. Wherein administration of ionizing radiation can be continuous, sequential or sporadic. Or an effect which would not be obtained if there is administered ionizing radiation without the separate, simultaneous or sequential administration of a compound of formula I, wherein administration can be continuous, sequential or sporadic.

Preferably combination refers to administration of an amount of a compound of formula I in combination with administration of an amount of ionizing radiation such that there is a synergistic antiproliferative effect and/or a clonogenic cell killing effect that would not be obtained if
  a. The compound of formula I is administered without prior, simultaneous or subsequent administration of ionizing radiation. Wherein administration can be continuous, sequential or sporadic;
  b. There is administration of ionizing radiation without the prior, simultaneous or subsequent administration of a compound of formula I. Where in administration can be continuous, sequential or sporadic.

The term "ionising radiation" referred to above and hereinafter means ionising radiation that occurs as either electromagnetic rays (such as X-rays and gamma rays) or particles (such as alpha and beta particles). Ionising radiation is provided in, but not limited to, radiation therapy and is known in the art (Hellman, Principles of Radiation Therapy, Cancer, in Principles and Practice of Oncology, 248-275 (Devita et al., ed., 4$^{th}$ Ed., V1, 1993).

In another combination of the invention, compounds of formula I and pharmaceutically acceptable salts and prodrug derivatives are preferably used in the form of pharmaceutical preparations that contain the relevant therapeutically effective amount of active ingredient optionally together with or in admixture with inorganic or organic, solid or liquid, pharmaceutically acceptable carriers which are suitable for administration.

In a preferred embodiment, each patient receives doses of ionizing radiation during the same period and the compound of formula I.

In an alternative embodiment, the ionizing radiation is given as a pre-treatment, i.e. before the treatment with the COMPOSITION OF THE INVENTION is started; the ionizing radiation alone is administered to the patient for a defined period of time, e.g. daily administration of the ionizing radiation alone for two or three days or weeks.

As mentioned above the precise dosage of the FLT-3 inhibitor to be employed for treating the diseases and conditions mentioned hereinbefore depends upon several factors including the host, the nature and the severity of the condition being treated, the mode of administration. However, in general, satisfactory results are achieved when the FLT-3 inhibitor is administered parenterally, e.g., intraperitoneally, intravenously, intramuscularly, subcutaneously, intratumorally, or rectally, or enterally, e.g., orally, preferably intravenously or, preferably orally, intravenously at a daily dosage of 0.1 to 10 mg/kg body weight, preferably 1 to 5 mg/kg body weight. In human trials a total dose of 225 mg/day was most presumably the Maximum Tolerated Dose (MTD). A preferred intravenous daily dosage is 0.1 to 10 mg/kg body weight or, for most larger primates, a daily dosage of 200-300 mg. A typical intravenous dosage is 3 to 5 mg/kg, three to five times a week.

Most preferably, the FLT-3 inhibitors, especially MIDOSTAURIN, are administered orally, by dosage forms such as microemulsions, soft gels or solid dispersions in dosages up to about 250 mg/day, in particular 225 mg/day, administered once, twice or three times daily.

Usually, a small dose is administered initially and the dosage is gradually increased until the optimal dosage for the host under treatment is determined. The upper limit of dosage is that imposed by side effects and can be determined by trial for the host being treated.

The FLT-3 inhibitor may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The infusion solutions according to the present invention are preferably sterile. This may be readily accomplished, e.g. by filtration through sterile filtration membranes. Aseptic formation of any composition in liquid form, the aseptic filling of vials and/or combining a pharmaceutical composition of the present invention with a suitable diluent under aseptic conditions are well known to the skilled addressee.

The FLT-3 inhibitor may be formulated into enteral and parenteral pharmaceutical compositions containing an amount of the active substance that is effective for treating the diseases and conditions named hereinbefore, such compositions in unit dosage form and such compositions comprising a pharmaceutically acceptable carrier.

Examples of useful compositions of FLT-3 inhibitors are described in the European patents No. 0 296 110, No. 0 657 164, No. 0 296 110, No. 0 733 372, No. 0 711 556, No. 0 711 557.

The preferred compositions of FLT-3 inhibitors are described in the European patent No. 0 657 164 published on Jun. 14, 1995. The described pharmaceutical compositions comprise a solution or dispersion of compounds of formula I such as MIDOSTAURIN in a saturated polyalkylene glycol glyceride, in which the glycol glyceride is a mixture of glyceryl and polyethylene glycol esters of one or more $C_8$-$C_{18}$ saturated fatty acids.

Two manufacture processes of such compositions of FLT-3 inhibitors are described hereafter.

Composition A:

Gelucire 44/14 (82 parts) is melted by heating to 60° C. Powdered MIDOSTAURIN (18 parts) is added to the molten material. The resulting mixture is homogenised and the dispersion obtained is introduced into hard gelatin capsules of different size, so that some contain a 25 mg dosage and others a 75 mg dosage of the MIDOSTAURIN. The resulting capsules are suitable for oral administration.

Composition B:

Gelucire 44/14 (86 parts) is melted by heating to 60° C. Powdered MIDOSTAURIN (14 parts) is added to the molten material. The mixture is homogenised and the dispersion obtained is introduced into hard gelatin capsules of different size, so that some contain a 25 mg dosage and others a 75 mg dosage of the MIDOSTAURIN. The resulting capsules are suitable for oral administration.

Gelucire 44/14 available commercially from Gattefossé; is a mixture of esters of C8-C18 saturated fatty acids with glycerol and a polyethylene glycol having a molecular weight of about 1500, the specifications for the composition of the fatty acid component being, by weight, 4-10% caprylic acid, 3-9% capric acid, 40-50% lauric acid, 14-24% myristic acid, 4-14% palmitic acid and 5-15% stearic acid.

A preferred example of Gelucire formulation consists of:
Gelucire (44/14): 47 g
MIDOSTAURIN: 3.0 g filled into a 60 mL Twist off flask A preferred example of soft gel will contain the following Microemulsion:

| | |
|---|---:|
| Cornoil glycerides | 85.0 mg |
| Polyethylen glykol 400 | 128.25 mg |
| Cremophor RH 40 | 213.75 mg |
| MIDOSTAURIN | 25.0 mg |
| DL alpha Tocopherol | 0.5 mg |
| Ethanol absolute | 33.9 mg |
| Total | 486.4 mg |

However, it should be clearly understood that it is for purposes of illustration only.

In particular, a therapeutically effective amount of each combination partner of the COMPOSITION OF THE INVENTION may be administered simultaneously or sequentially and in any order, and the components may be administered separately or as a fixed combination. For example, the method of delay of progression or treatment of a proliferative disease according to the invention may comprise (i) administration of the first combination partner and (ii) administration of the second combination partner, wherein administration of a combination partner may be simultaneous or sequential in any order, in jointly therapeutically effective amounts, preferably in synergistically effective amounts, e.g. in daily or weekly dosages corresponding to the amounts described herein. The individual combination partners of the COMPOSITION OF THE INVENTION can be administered separately at different times during the course of therapy or concurrently. Furthermore, the term administering also encompasses the use of a pro-drug of a compound of formula I that converts in vivo to the combination partner as such. The instant invention is therefore to be understood as embracing all such regimes of simultaneous or alternating treatment and the term "administering" is to be interpreted accordingly.

The dosage of ionizing radiation and a compound of formula I in relation to each other is preferably in a ratio that is synergistic.

The particular mode of administration and the dosage of a compound of formula I may be selected by the attending physician taking into account the particulars of the patient, especially age, weight, life style, activity level, etc.

The dosage of a compound of formula I may depend on various factors, such as effectiveness and duration of action of the active ingredient, mode of administration, effectiveness and duration of action of the ionizing radiation and/or sex, age, weight and individual condition of the subject to be treated.

The dosage of ionizing radiation may depend on various factors, such as effectiveness and duration of action of the ionizing radiation, mode of administration, location of administration, effectiveness and duration of action of the compound of formula I and/or sex, age, weight and individual condition of the subject to be treated. The dosage of ionizing radiation is generally defined in terms of radiation absorbed dose, time and fraction, and must be carefully defined by the attending physician.

In one preferred embodiment of the invention the combination comprises N-[(9S,10R,11R,13R)-2,3,10,11,12,13-hexahydro-10-methoxy-9-methyl-1-oxo-9,13-epoxy-1H, 9H-diindolo[1,2,3-gh:3',2',1'-lm]pyrrolo[3,4-j][1,7]benzodiazonin-11-yl]-N-methylbenzamide of the formula (VII):

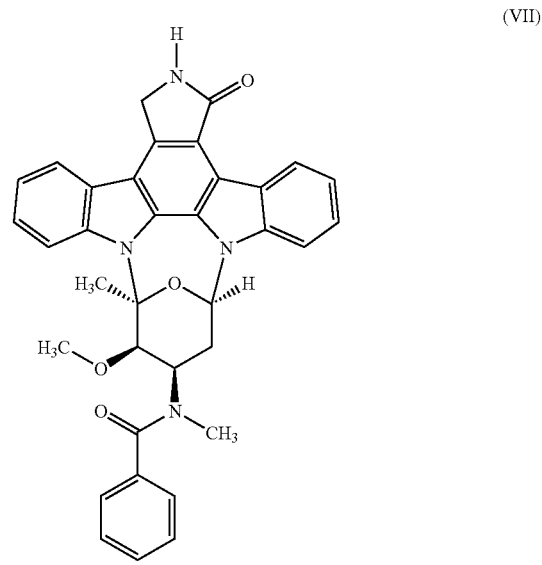

(VII)

or a salt thereof.

Moreover, the present invention relates to a method of treating a warm-blooded animal having a proliferative disease comprising administering to the animal a COMPOSITION OF THE INVENTION in a way that is jointly therapeutically effective against a proliferative disease and in which the combination partners can also be present in the form of their pharmaceutically acceptable salts.

Furthermore, the present invention pertains to the use of a COMPOSITION OF THE INVENTION for the delay of progression or treatment of a proliferative disease and for the preparation of a medicament for the delay of progression or treatment of a proliferative disease.

In one embodiment of the invention, an antidiarrheal agent is administered together with the COMPOSITION OF THE INVENTION in order to prevent, control or eliminate diarrhoea that is sometimes associated with the administration of a compound of formula I. Thus, the present invention also relates to a method of preventing or controlling diarrhoea associated with administering a compound of formula I, which comprises administering an effective amount of an antidiarrhea agent to the patient receiving treatment with the COMPOSITION OF THE INVENTION. Antidiarrheal agents and protocols for their administration are known to those skilled in the art. Antidiarrheal agents suitable for use in the inventive methods and compositions include, but are not limited to, natural opiods, such as tincture of opium, paregoric, and codeine, synthetic opioids, such as diphenoxylate, difenoxin and loperamide, bismuth subsalicylate, octreotide (e.g. available as SANDO-STATINTM), motilin antagonists and traditional antidiarrheal remedies, such as kaolin, pectin, berberine and muscarinic agents.

The following example is intended to illustrate the invention and are not to be construed as being limitations thereon.

EXAMPLE 1

Products of chromosomal translocations play a crucial role both in the oncogenic process and as targets for therapeutic intervention. However, unlike BCR/ABL whose kinase activity can be specifically inhibited by a small molecule (Glivec), most chromosomal translocations upregulate native or generate chimeric oncogenic transcription factors which in general are less amendable to small molecule inhibition.

Recently, we have established a gene signature characteristic for the Pediatric sarcoma alveolar rhabdomyosarcoma (aRMS), which expresses the chimaeric fusion protein PAX3/FKHR due to a chromosomal translocation event t(2; 13). Based on this signature, a number of potential therapeutic target molecules have been selected for further study, such as FGFR2. Here, we now demonstrate that PKC412, a staurosporine derivative originally developed against PKC, can efficiently inhibit cell growth of aRMS cells in vitro and induce apoptosis due to enhanced caspase 3 activity. Furthermore, tumor growth could also be inhibited in vivo using a mouse xenograft tumor model.

Because specific downregulation of PAX3/FKHR by either siRNA or antisense oligonucleotides can similarly induce apoptosis in aRMS cells, we investigated any potential effects of PKC412 on PAX3/FKHR by analyzing expression of specific target genes such as CB1. Interestingly, CB1 expression was completely abolished upon treatment with PKC412 suggesting that the compound regulates the activity of PAX3/FKHR. Surprisingly, this inhibition was also observed with PAX3/NCOA1, which thus suggests that the PAX3 part of the fusion proteins is the target of the inhibitory function of PKC412. Finally, we identified several phosphorylation sites in the PAX3 region which potentially act as regulators of its activity.

These experiments suggest that treatment of aRMS with PKC412 leads to induction of apoptotic cell death and tumor growth inhibition in vitro and in vivo, likely mediated via inhibition of the activity of PAX3/FKHR, a chimaeric oncogenic transcription factor.

The invention claimed is:

1. A method for the treatment of Alveolar Rhabdomyosarcoma associated with a PAX/FKHR translocation, which comprises administering a therapeutically effective amount of N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide.

2. A method according to claim 1, wherein the PAX/FKHR translocation is selected from a PAX3/FKHR translocation and a PAX7/FKHR translocation.

3. A method according to claim 2, wherein the PAX/FKHR translocation is a PAX3/FKHR translocation.

* * * * *